United States Patent
Sumida et al.

(10) Patent No.: US 9,889,285 B2
(45) Date of Patent: Feb. 13, 2018

(54) OPERATION TOOL FOR FLUID INJECTOR USING MULTI-MICRONEEDLE DEVICE

(71) Applicant: TOPPAN PRINTING CO., LTD., Taito-ku (JP)

(72) Inventors: Tomoya Sumida, Taito-ku (JP); Yumiko Ikeda, Taito-ku (JP); Masaki Kono, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 573 days.

(21) Appl. No.: 14/605,436

(22) Filed: Jan. 26, 2015

(65) Prior Publication Data

US 2015/0133866 A1    May 14, 2015

Related U.S. Application Data

(63) Continuation of application No. PCT/JP2013/070108, filed on Jul. 24, 2013.

(30) Foreign Application Priority Data

Jul. 25, 2012 (JP) ................................ 2012-164703

(51) Int. Cl.
   *A61M 37/00* (2006.01)
   *A61M 5/315* (2006.01)
   (Continued)

(52) U.S. Cl.
   CPC .... *A61M 37/0015* (2013.01); *A61M 5/31576* (2013.01); *A61B 17/205* (2013.01); *A61M 5/3287* (2013.01); *A61M 2037/0023* (2013.01)

(58) Field of Classification Search
   CPC .......... A61M 37/0015; A61M 5/31576; A61M 2037/0023; A61M 2037/003;
   (Continued)

(56) References Cited

U.S. PATENT DOCUMENTS

2007/0038181 A1* 2/2007 Melamud ........... A61B 17/3478
                                                              604/158
2008/0027384 A1    1/2008 Wang et al.
(Continued)

FOREIGN PATENT DOCUMENTS

EP    2 460 553 A1    6/2012
JP    2010-518951     6/2010
(Continued)

OTHER PUBLICATIONS

International Search Report dated Oct. 22, 2013, in in Application No. PCT/JP2013/070108.
(Continued)

*Primary Examiner* — Imani Hayman
*Assistant Examiner* — Nilay Shah
(74) *Attorney, Agent, or Firm* — Oblon, McClelland, Maier & Neustadt, L.L.P.

(57) ABSTRACT

An operation tool includes a mechanism sequentially moving the injector in a space of an outer cylinder among an initial position in which needles of a main body of the device are retracted inside the space, a first position in which the needles protrude to the outside by a first distance, and a second position in which needles protrude to the outside by a second distance shorter than the first distance. Fluid flows from the injector through the needles in the second position. The mechanism has a unit forcing the injector toward the initial position by a magnetic force, first and second stoppers which can be selectively extended/retracted with respect to the outer peripheral wall of the outer cylinder, and an engaging portion which is selectively engaged with these stoppers on the outer peripheral wall of the injector and selectively arranging the injector in the above three positions.

10 Claims, 5 Drawing Sheets

(51) Int. Cl.
*A61M 5/32* (2006.01)
*A61B 17/20* (2006.01)

(58) Field of Classification Search
CPC ........... A61M 2037/0061; A61M 2005/14252; A61M 2005/14284; A61M 2005/206; A61M 5/3287; A61M 2005/2488; A61M 5/2429; A61B 17/205; A61B 5/150175; A61B 5/150183; A61B 5/15019
See application file for complete search history.

(56) References Cited

U.S. PATENT DOCUMENTS

| | | | |
|---|---|---|---|
| 2008/0200863 A1 | 8/2008 | Chomas et al. | |
| 2009/0043324 A1* | 2/2009 | Paschal | A61B 5/1411 606/181 |
| 2010/0121271 A1 | 5/2010 | Perriere | |
| 2014/0296825 A1 | 10/2014 | Lemaire et al. | |
| 2016/0339179 A1 | 11/2016 | Lemaire et al. | |

FOREIGN PATENT DOCUMENTS

| | | |
|---|---|---|
| JP | 2010-532219 | 10/2010 |
| JP | 2012-100783 | 5/2012 |
| WO | 2009/107806 | 9/2009 |
| WO | 2009/130926 | 10/2009 |

OTHER PUBLICATIONS

U.S. Appl. No. 14/584,213, filed Dec. 29, 2014, Sumida, et al.
U.S. Appl. No. 14/689,541, filed Apr. 17, 2015, Sumida, et al.
Office Action dated Apr. 11, 2017 in Japanese Patent Application No. 2014-526982 (with English translation).

* cited by examiner

OPERATION TOOL FOR FLUID INJECTOR USING MULTI-MICRONEEDLE DEVICE

CROSS-REFERENCE TO RELATED APPLICATIONS

The present application is a continuation of International Application No. PCT/JP2013/070108, filed Jul. 24, 2013, which is based upon and claims the benefits of priority to Japanese Application No. 2012-164703, filed Jul. 25, 2012. The entire contents of these applications are incorporated herein by reference.

BACKGROUND OF THE INVENTION

Technical Field

The present invention relates to an operation tool for a fluid injector using a multi-microneedle device.

Background Art

The fluid injector using the multi-microneedle device is known, for example, in a medical field. Such fluid injector in the medical field is known as a syringe.

The fluid injector includes a fluid holding cylinder (an injection cylinder in the syringe) having a long fluid holding space capable of holding a given amount of fluid (for example, liquid medicine in the medical field), a fluid outflow port arranged at one end of a longitudinal direction of the fluid holding space, from which the fluid in the fluid holding space can flow, and a fluid holding space inlet opening arranged at the other end of the longitudinal direction of the fluid holding space. The fluid injector further includes a piston member incorporated with the fluid holding space of the fluid holding cylinder so as to slide along the center line of the longitudinal direction through the fluid holding space inlet opening.

SUMMARY OF INVENTION

According to one aspect of the present invention, an operation tool for a fluid injector having a multi-microneedle device, includes an outer cylinder including a first open end, a second open end and a housing extending from the first open end to the second open end, the housing being formed such that a fluid injector having a multi-microneedle device is movable in the housing along a central line in a longitudinal direction of the fluid injector; and a selective movement mechanism which moves the fluid injector from an initial position to a first protruding position and then to a second protruding position in the housing of the outer cylinder. When the fluid injector is at the initial position, the multi-microneedle device has a plurality of microneedles retracted from the first open end of the outer cylinder and positioned inside the housing. When the fluid injector is at the first protruding position, the microneedles are protruded out to a first distance from the first open end. When the fluid injector is at the second protruding position to discharge fluid through the microneedles of the multi-microneedle device, the microneedles are protruded out to a second distance from the first open end, the second distance being shorter than the first distance. The selective movement mechanism includes: a forcing unit which is interposed between the outer cylinder and the fluid injector and applies a magnetic force to the fluid injector toward the initial position; a first stopper positioned at a first position on an outer peripheral wall of the outer cylinder such that the first stopper is selectively extended into or retracted from the housing, the first position being at a distance away from the first open end toward the second open end; a second stopper positioned at a second position on the outer peripheral wall of the outer cylinder such that the second stopper is selectively extended into or retracted from the housing, the second position being at a distance away from the first position and toward the second open end; and an engaging portion provided on an outer peripheral wall of the fluid injector and protruding toward the outer peripheral wall of the outer cylinder. When the first and second stoppers are retracted from the housing, the engaging portion of the fluid injector is not engaged with the first and second stoppers and at an initial position by a force of the forcing unit. When the first stopper is extended into the housing after the fluid injector is moved to the first protruding position against the force of the forcing unit, the engaging portion is engaged with the first stopper and the fluid injector is held in the first protruding position against the force of the forcing unit. When the first stopper is retracted from the housing and the second stopper is extended into the housing after the fluid injector is moved to the first protruding position against the force of the forcing unit, the engaging portion is engaged with the second stopper and the fluid injector is held at the second protruding position against the force of the forcing unit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
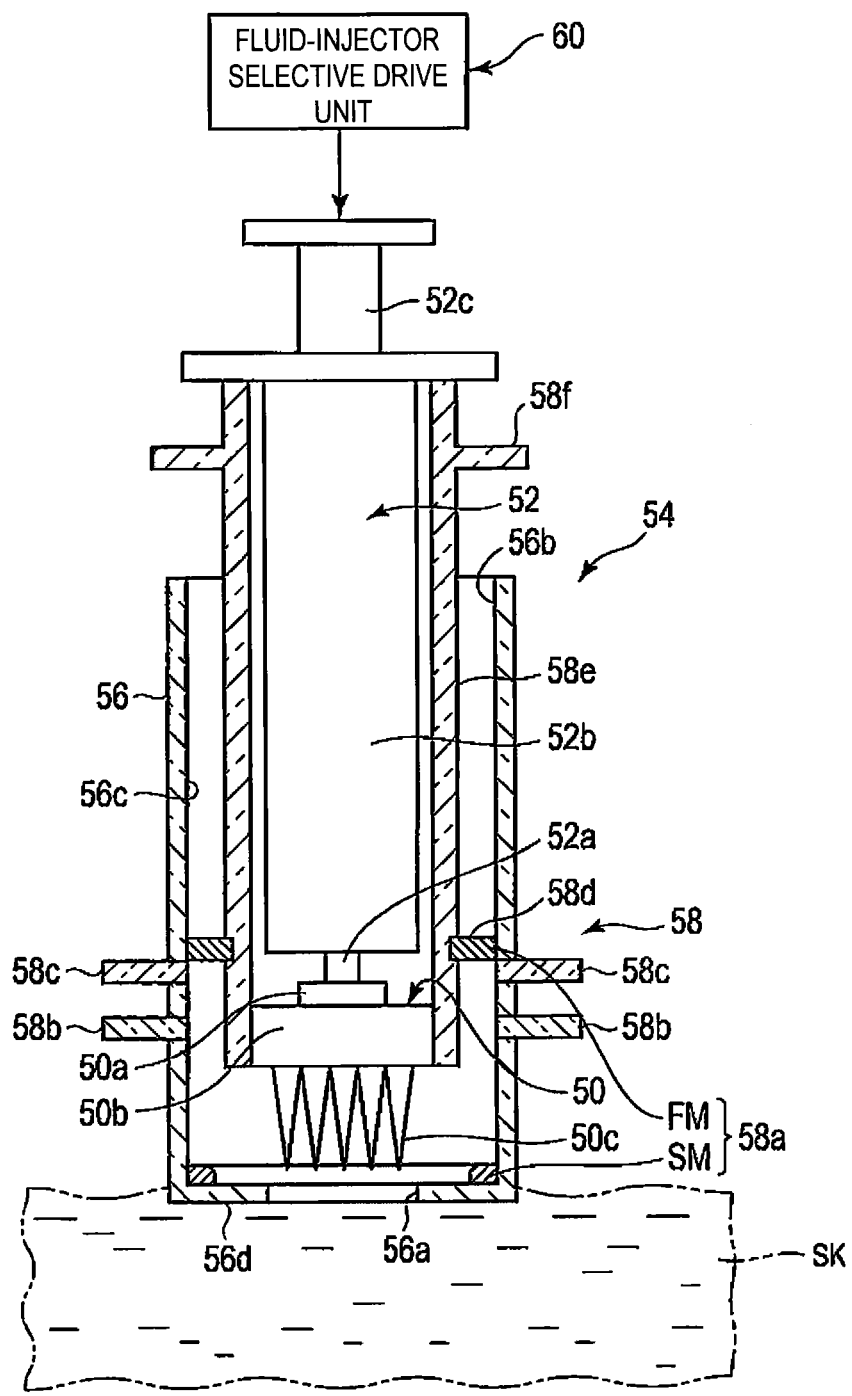
FIG. 1 is a schematic vertical-cross sectional view of an operation tool for a fluid injector using a multi-microneedle device according to an embodiment, in which the fluid injector using the multi-microneedle device is arranged in an initial position by a selective movement mechanism in an outer cylinder of the operation tool.

The embodiments will now be described with reference to the accompanying drawings, wherein like reference numerals designate corresponding or identical elements throughout the various drawings.

First Embodiment

A structure of an operation tool 54 according to an embodiment for a fluid injector 52 using a multi-microneedle device 50 will be schematically explained with reference to FIG. 1 to FIG. 3.

The fluid injector 52 using the multi-microneedle device 50 operated by the operation tool 54 according to the embodiment is considered to be used as, for example, a syringe in a medical field.

The fluid injector 52 includes a fluid holding cylinder 52*b* (an injection cylinder in the syringe) having a long fluid holding space capable of holding a given amount of fluid (for example, liquid medicine in the medical field), a fluid outflow port 52*a* arranged at one end of a longitudinal direction of the fluid holding space, from which the fluid in the fluid holding space can flow, and a fluid holding space inlet opening arranged at the other end of the longitudinal direction of the fluid holding space. The fluid injector 52 further includes a piston member 52*c* incorporated with the fluid holding space of the fluid holding cylinder 52*b* so as to slide along the center line of the longitudinal direction through the fluid holding space inlet opening.

The multi-microneedle device 50 in the medical field is considered to be used in an intradermal injection by being attached to the fluid outflow port of the injection cylinder in the conventional syringe instead of one injection needle which is well-known in the medical field.

The multi-microneedle device 50 includes a main body 50*b* which is provided with an outflow-port attaching port 50*a* attached to the fluid outflow port 52*a* of the fluid (liquid medicine in the medical field) of the fluid holding cylinder 52*b* (the injection cylinder in the syringe) of the fluid injector 52 so as to be detachable and a fluid holding space temporarily holding the fluid flowing from the fluid outflow port 52*a* of the fluid holding cylinder 52*b* to the outflow-port attaching port 50*a* by pressing the piston member 52*c* of the fluid injector 52, and a plurality of microneedles 50*c* arranged on a surface (a flat surface in the embodiment) positioned on the opposite side of the outflow-port attaching port 50*a* interposing the fluid holding space in the main body 50*b*.

The multi-microneedle device 50 can be fabricated by applying, for example, an etching process using a well-known photolithography method on a silicon substrate. It is also possible to fabricate a replication model having a reversal shape by an electroforming by using the multi-microneedle device made of silicon as an original model and to form a multi-microneedle device made of resin based on the replication model.

In the multi-microneedle device 50, at least plural microneedles 50*c* are preferably made of a biocompatible material, and it is further preferable that the entire multi-microneedle device 50 is made of the biocompatible material. As biocompatible materials, for example, metals such as stainless steel, titanium and manganese, resins such as medical silicone, polylactic acid, polyglycolic acid and polycarbonate and inorganic materials such as silicon are included.

The above-described biocompatible resin materials can be processed to at least plural microneedles 50*c* of the multi-microneedle device 50 or the entire multi-microneedle device 50 by using well-known molding techniques such as injection molding, imprinting, hot-embossing and casting.

The respective plural microneedles 50*c* have small fluid injection passages extending between a base end on the flat surface and tip ends apart from the flat surface. A length between the base end and the tip ends in respective plural microneedles 50*c*, namely, the height of each microneedle 50*c* is set to be in a range of the thickness of the skin tissue of living things (for example, all human beings) having skin tissue to be targets for use, which is preferably in a range of the thickness of the skin tissue not including nerves. Specifically, the height of the microneedles 50*c* is preferably set to be in a range from 100 to 2000 µm.

The entire shape of respective plural microneedles 50*c* can be cone shapes including a circular cone and a pyramid, columns or prisms with tip portions having a cone shape or a pyramid shape. The small fluid outflow passages with respect to respective plural microneedles 50*c* can be formed by well-known small-hole drilling processes using, for example, a micro drill, a laser beam and so on.

The arrangement of plural microneedles 50*c* on the flat surface of the main body 50*b* can be in a lattice shape, a concentric-circle shape, a random shape or the like.

The operation tool 54 according to the embodiment includes an outer cylinder 56 having one end opening 56*a*, the other end opening 56*b* and a fluid-injector housing space 56*c* extending between the one end opening 56*a* and the other end opening 56*b* and holding the fluid injector 52 using the multi-microneedle device 50 so as to move along the center line of the longitudinal direction of the fluid injector 52.

The operation tool 54 according to the embodiment also includes a selective movement mechanism 58 sequentially moving the fluid injector 52 among an initial position, a first protruding position and a second protruding position in the fluid-injector housing space 56*c* of the outer cylinder 56.

The selective movement mechanism 58 in the operation tool 54 according to the embodiment is configured to recover the fluid injector 52 in the fluid-injector housing space 56*c* of the outer cylinder 56 to the initial position after the second protruding position.

In the initial position, the fluid injector 52 allows the plural microneedles 50*c* of the multi-microneedle device 50 to be retracted inside the fluid-injector housing space 56*c* from the one end opening 56*a* of the outer cylinder 56 as shown in FIG. 1.

Figure 2:
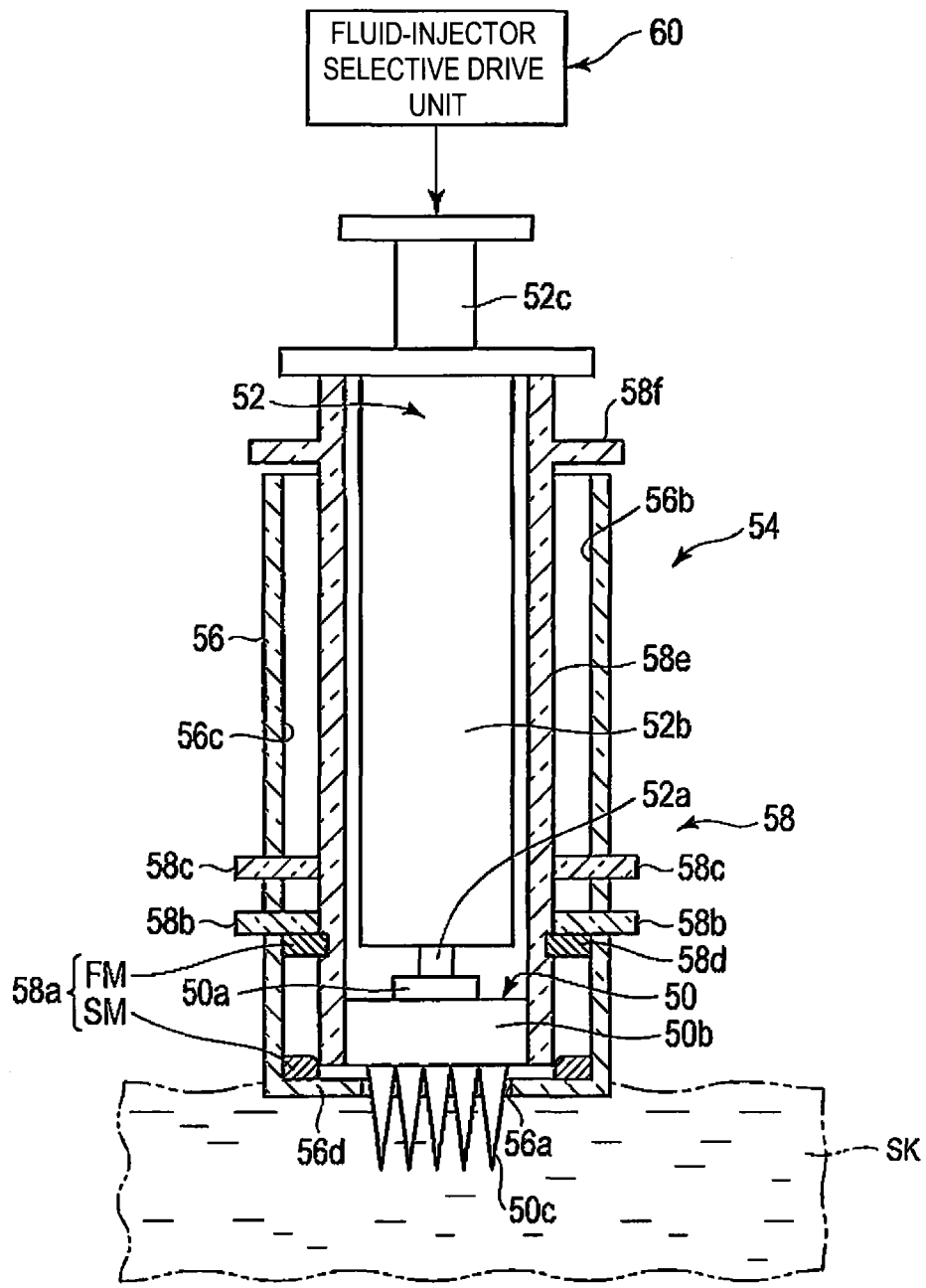
FIG. 2 is a schematic vertical-cross sectional view of the operation tool for the fluid injector using the multi-microneedle device according to the embodiment, in which the fluid injector using the multi-microneedle device is arranged in a first protruding position by the selective movement mechanism in the outer cylinder of the operation tool.

In the first protruding position, the fluid injector 52 allows the plural microneedles 50*c* of the multi-microneedle device 50 to protrude to an outer space from the one end opening 56*a* of the outer cylinder 56 by a first given distance as shown in FIG. 2.

Figure 3:
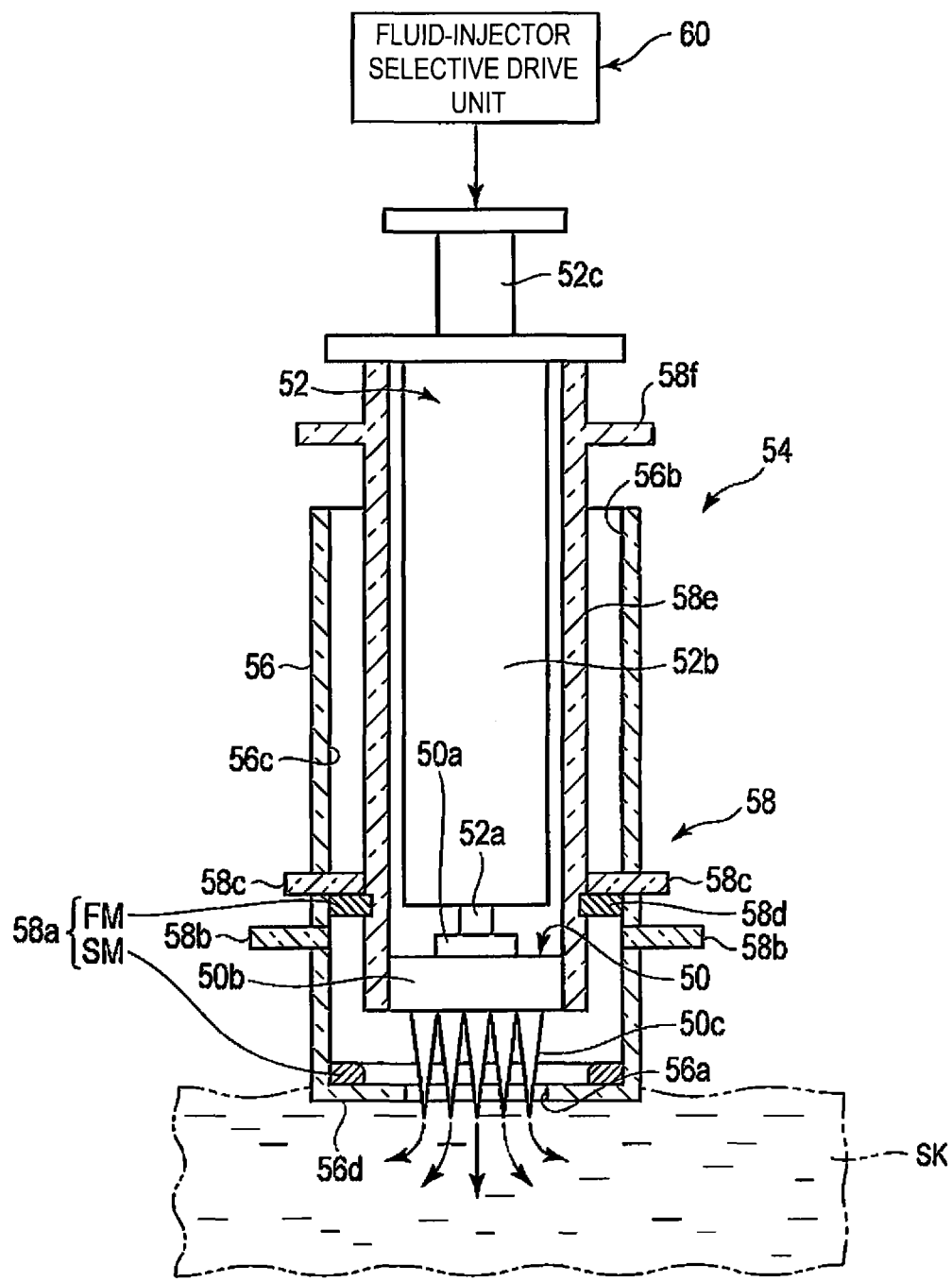
FIG. 3 is a schematic vertical-cross sectional view of the operation tool for the fluid injector using the multi-microneedle device according to the embodiment, in which the fluid injector using the multi-microneedle device is arranged in a second protruding position by the selective movement mechanism in the outer cylinder of the operation tool.

In the second protruding position, the fluid injector 52 allows the plural microneedles 50*c* of the multi-microneedle device 50 to protrude to the outer space from the one end opening 56*a* of the outer cylinder 56 by a second given distance shorter than the first given distance as shown in FIG. 3.

In the operation tool 54 according to the embodiment, the fluid flows from the fluid injector 52 through the plural microneedles 50*c* of the multi-microneedle device 50 in the second protruding position.

In the embodiment, the one end opening 56*a* of the outer cylinder 56 is an opening having a given diameter formed in a central portion of an end wall formed in one end of the outer cylinder 56 and an outer surface of the end wall of the outer cylinder 56 functions as a skin contact surface 56d.

The selective movement mechanism 58 of the operation tool 54 according to the embodiment includes a forcing unit 58a interposed between the outer cylinder 56 and the fluid injector 52, forcing the fluid injector 52 toward the above-described initial position shown in FIG. 1 by a magnetic force.

The selective movement mechanism 58 of the operation tool 54 according to the embodiment also includes a first stopper 58b provided in a first position a given distance apart from the one end opening 56a of the end wall toward the inside in an outer peripheral wall of the outer cylinder 56 so as to be extended/retracted selectively with respect to the fluid-injector housing space 56c of the outer cylinder 56. The first stopper 58b is provided in the first position of the outer peripheral wall of the outer cylinder 56 so as to be extended/retracted selectively with respect to the fluid-injector housing space 56c by, for example, a well-known sliding mechanism or a well-known rotation mechanism.

The selective movement mechanism 58 of the operation tool 54 according to the embodiment also includes a second stopper 58c provided in a second position a given distance apart from the one end opening 56a of the end wall as compare with the first position toward the inside in the outer peripheral wall of the outer cylinder 56 so as to be extended/retracted selectively with respect to the fluid-injector housing space 56c of the outer cylinder 56. The second stopper 58c is provided in the second position of the outer peripheral wall of the outer cylinder 56 so as to be extended/retracted selectively with respect to the fluid-injector housing space 56c by, for example, a well-known sliding mechanism or a well-known rotation mechanism.

The selective movement mechanism 58 of the operation tool 54 according to the embodiment further includes an engaging portion 58d protruding toward the outer peripheral wall of the outer cylinder 56 in the outer peripheral wall of the fluid injector 52.

More specifically, the selective movement mechanism 58 includes a cylindrical intermediate member 58e having one end opening and the other end opening, which is arranged between the outer peripheral wall of the outer cylinder 56 and an outer peripheral of the fluid holding cylinder 52b (the injection cylinder in the syringe) of the fluid injector 52 having the multi-microneedle device 50. An outer peripheral surface of the main body 50b of the multi-microneedle device 50 of the fluid injector 52 is fixed to the one end opening of the cylindrical intermediate member 58e, and the fluid injector 52 connected to the multi-microneedle device 50 is housed inside a columnar space extending between the one end opening and the other end opening of the intermediate member 58e. The intermediate member 58e can be moved with respect to the center line of the longitudinal direction of the outer cylinder 56 together with the fluid injector 52 having the multi-microneedle device 50 inside the fluid-injector housing space 56c of the outer cylinder 56, and the engaging portion 58d is fixed to the outer peripheral wall of the intermediate member 58e.

Concerning the main body 50b of the multi-microneedle device 50 and the intermediate member 58e, the main body 50b of the multi-microneedle device 50 can be fixed to the intermediate member 58e by well-known fixing structures such as an adhesive, snap engagement and a fixing screw after being formed separately, or the multi-microneedle device 50 and the intermediate member 58e can be integrally formed at the same time.

The intermediate member 58e and the engaging portion 58d can be fixed to each other by well-known fixing structures such as the adhesive, the snap engagement and the fixing screw after being formed separately, or the intermediate member 58e and the engaging portion 58d can be integrally formed at the same time.

That is, the engaging portion 58d according to the embodiment protrudes from the outer peripheral wall of the fluid injector 52 toward the outer peripheral wall of the outer cylinder 56 through the intermediate member 58e and the multi-microneedle device 50.

The forcing unit 58a includes a first magnetic force holding body FM provided in the engaging portion 58d of the outer peripheral wall of the fluid injector 52 and a second magnetic force holding body SM arranged in the outer cylinder 56 so as to generate a repulsion due to the magnetic force with respect to the first magnetic force holding body FM.

The first magnetic force holding body FM and the second magnetic force holding body SM can be respectively magnets, can be magnetic bodies processed to hold the magnetic force and can be permeability magnetic materials into which small pieces or fine grains of magnets or magnetic bodies processed to hold the magnetic force are mixed.

The entire engaging portion 58d on the outer peripheral wall of the fluid injector 52 can be made of the first magnetic force holding body FM or part of the engaging portion 58d can be made of the first magnetic force holding body FM.

It is preferable that the engaging portion 58d is provided at least at one place on the outer peripheral wall of the fluid injector 52 as well as at plural places annularly arranged on the outer peripheral wall, and further, the entire engaging portion 58d may have an annular shape.

It is preferable that the second magnetic force holding body SM is provided at least at one place on the outer cylinder 56 as well as at plural places annularly arranged on the outer cylinder, and further, the entire second magnetic force holding body SM may have an annular shape.

In the embodiment, the second magnetic force holding body SM has the annular shape, which is fixed by well-known fixing means such as the adhesive, the snap engagement and the fixing screw around the one end opening 56a on an inner peripheral surface of the outer cylinder 56 so as to be opposite to the engaging portion 58d on the outer peripheral wall of the fluid injector 52.

As shown in FIG. 1, while the first stopper 58b and the second stopper 58c are arranged at the position retracted from the outer cylinder 56, the fluid injector 52 connected to the multi-microneedle device 50 is arranged in the above-described initial position with the intermediate member 58e by the repulsion (biasing force) due to the magnetic force by the forcing unit 58a. Here, the engaging portion 58d of the fluid injector 52 is positioned in an inner side of the first stopper 58b and the second stopper 58c on the outer peripheral wall of the outer cylinder 56 with respect to the one end opening 56c of the outer cylinder 56.

The other end portion having the other end opening on the outer peripheral wall of the intermediate member 58e protrudes from the other end opening 56b of the outer cylinder 56 to the outer space while the fluid injector 52 is arranged in the above-described initial position as shown in FIG. 1. In the other end portion on the outer peripheral wall of the intermediate member 58e, an intermediate member operation protrusion 58f is formed, which is for assisting a user to move the intermediate member 58e relatively with respect to the center line of the longitudinal direction of the outer cylinder 56 in the fluid-injector housing space 56c of the outer cylinder 56.

The other end portion of the fluid holding cylinder 52b (the injection cylinder in the syringe) of the fluid injector 52 which is connected to the multi-microneedle device 50 and the piston member 52c protrude to the outer space from the other end opening of the intermediate member 58e.

The outer cylinder 56, the intermediate member 58e and the fluid holding cylinder 52b (the injection cylinder in the syringe) of the fluid injector 52 in the embodiment are preferably made of a transparent material respectively so that an amount of fluid (liquid medicine in the medical field) held by the fluid holding cylinder 52b can be visually recognized from the outside of the outer cylinder 56. In each of the outer cylinder 56 and the intermediate member 58e, only portions corresponding to the fluid holding cylinder 52b of the fluid injector 52 in respective outer peripheral walls can be made of the transparent material.

Next, procedures in which the fluid (for example, liquid medicine) held by the fluid injector 52 is injected into skin tissue at an exposed desired place of the skin of a living thing (for example, a human being in the embodiment) by operating the fluid injector 52 using the multi-microneedle device 50 by the operation tool 54 according to the embodiment will be explained with reference to FIG. 1 to FIG. 3.

First, the user of the operation tool 54 according to the embodiment attaches the fluid outflow port 52a of the fluid holding cylinder 52b of the fluid injector 52 to the outflow-port attaching port 50a of the multi-microneedle device 50 so as to be detachable while the first stopper 58b and the second stopper 58c of the selective movement mechanism 58 are arranged in the retracted position as shown in FIG. 1 and the intermediate member 58e having the multi-microneedle device 50 is arranged in the initial position as shown in FIG. 1 by the repulsion (biasing force) due to the magnetic force by the forcing unit 58a.

At this time, plural microneedles 50c of the multi-microneedle device 50 arranged in the initial position as described above are retracted inside the fluid-injector housing space 56c of the outer cylinder 56 from the one end opening 56a of the outer cylinder 56.

Furthermore, the fluid (for example, liquid medicine) to be injected into the skin tissue of the living thing (for example, the human being) is already filled in the fluid holding cylinder 52b of the fluid injector 52, and by slightly pushing the piston member 52c, the fluid held by the fluid holding cylinder 52b is allowed to flow into the fluid holding space of the main body 50b of the multi-microneedle device 50 and small fluid injection passages of the plural microneedles 50c of the multi-microneedle device 50, which are filled with the fluid.

After that, the user grasps the outer peripheral surface of the outer cylinder 56 so as not to touch the first stopper 58b and the second stopper 58c in the retracted position of the selective movement mechanism 58 and sequentially presses the skin contact surface 56d of the outer surface in the end surface of one end wall of the outer cylinder 56 as shown in FIG. 1 onto an exposed desired position of a skin SK of the living thing (for example, the human being).

At this time, the exposed desired position of the skin SK is pressed toward the inside of the skin SK by the skin contact surface 56d of the end wall of the outer cylinder 56.

Next, the user pushes the intermediate member operation protrusion 58f of the intermediate member 58e to move the intermediate member 58e toward the end wall of the outer cylinder 56 against the repulsion (biasing force) due to the magnetic force of the forcing unit 58a until the engaging portion 58d of the intermediate member 58e passes the second stopper 58c and the first stopper 58b in the retracted position.

After that, the second stopper 58c and the first stopper 58b are moved to the protruding position as shown in FIG. 2, and the pressing with respect to the intermediate member operation protrusion 58f of the intermediate member 58e is cancelled. As a result, the intermediate member 58e to which the multi-microneedle device 50 is fixed is to return to the initial position of FIG. 1 by the repulsion (biasing force) due to the magnetic force by the forcing unit 58a, however, the engaging portion 58d of the intermediate member 58e is engaged with the first stopper 58b in the protruding position as shown in FIG. 2, therefore, the intermediate member 58e to which the multi-microneedle device 50 is fixed holds the multi-microneedle device 50 in the first protruding position against the repulsion (biasing force) due to the magnetic force by the forcing unit 58a.

The plural microneedles 50c of the multi-microneedle device 50 moved from the initial position shown in FIG. 1 to the first protruding position shown in FIG. 2 as described above protrude from the one end opening 56a of the outer cylinder 56 to the outside by the first given distance. At this time, the plural microneedles 50c positively pierce a region surrounded by the one end opening 56a of the end wall of the outer cylinder 56 as shown in FIG. 2 in the exposed desired position of the skin SK pressed by the skin contact surface 56d of the end wall of the outer cylinder 56.

At this time, the elasticity of skin tissue in the region of the exposed desired position of the skin SK is somewhat lost.

Subsequently, the first stopper 58b of the selective movement mechanism 18 moves to the retracted position as shown in FIG. 3. As a result, the intermediate member 58e to which the multi-microneedle device 50 is fixed is to return to the initial position of FIG. 1 by the repulsion (biasing force) due to the magnetic force by the forcing unit 58a, however, the engaging portion 58d of the intermediate member 58e is engaged with the second stopper 58c in the protruding position as shown in FIG. 3, therefore, the intermediate member 58e to which the multi-microneedle device 50 is fixed holds the multi-microneedle device 50 in the second protruding position against the repulsion (biasing force) due to the magnetic force by the forcing unit 58a.

The plural microneedles 50c of the multi-microneedle device 50 moved from the first protruding position shown in FIG. 2 to the second protruding position shown in FIG. 3 protrude from the one end opening 56a of the outer cylinder 56 by the second given distance shorter than the first given distance.

The plural microneedles 50c of the multi-microneedle device 50 moved to the second protruding position reduce a pressing force with respect to the region surrounded by the one end opening 56a of the outer cylinder 56 in the exposed desired position of the skin SK, however, the region follows the plural microneedles 50c as the elasticity in the region is recovered, as a result, the piercing of the plural microneedles 50c with respect to the region as shown in FIG. 3 is maintained.

While the multi-microneedle device 50 is held in the second protruding position shown in FIG. 3 as described above, the user presses the piston member 52c of the fluid injector 52. As a result, the fluid filled in the fluid holding cylinder 52b of the fluid injector 52, the fluid holding space of the main body 50b of the multi-microneedle device 50 and the small fluid injection passages of the plural microneedles 50c as described above can be injected easily and quickly into the skin tissue of the region at the exposed desired position of the skin SK in which the elasticity is recovered as described above without leaking the fluid to the outside of the skin SK as shown by plural arrows in FIG. 3 through the small fluid injection passages of the plural microneedles 50c of the multi-microneedle device 50 in accordance with the distance of pressing.

At this time, the user can hold the other end portion of the intermediate member 58e or the other end portion of the fluid holding cylinder 52b, or can move the first stopper 58b to the protruding position again so as to eliminate the possibility that the plural microneedles 50c of the multi-microneedle device 50 moves with the fluid holding cylinder 52b and the intermediate member 58e from the second protruding position shown in FIG. 3 toward the first protruding position shown in FIG. 2 by pressing the piston member 52c.

When the outer cylinder 56 and the intermediate member 58e of the operation tool 54 as well as the fluid holding cylinder 52b of the fluid injector 52 are made of the transparent material as described above, the user can easily check the injection amount of fluid by visually confirming the injection amount through the outer cylinder 56 and the intermediate member 58e of the operation tool 54 as well as the fluid holding cylinder 52b of the fluid injector 52.

After the fluid injection from the fluid injector 52 into the skin tissue of the region at the exposed desired position of the skin SK through the plural microneedles 50c of the multi-microneedle device 50 is completed, the operation tool 54 is separated from the exposed desired position of the skin SK, and the multi-microneedle device 50 is pulled out of the skin tissue of the region at the exposed desired position of the skin SK at the same time.

Before or after the operation tool 54 is separated from the exposed desired position of the skin SK, the second stopper 58c is moved to the retracted position. As a result, the intermediate member 58e to which the multi-microneedle device 50 is fixed is returned to the initial position in FIG. 1 by the repulsion (biasing force) of magnetic force of the forcing unit 58a.

Furthermore, in the above embodiment, the user presses the piston member 52c exposed to the outside of the fluid injector 52 while the plural microneedles 50c of the multi-microneedle device 50 are held in the second protruding position as shown in FIG. 3. However, the pressing of the piston member 52c while the plural microneedles 50c of the multi-microneedle device 50 are held in the second protruding position can be performed by a fluid-injector selective drive unit 60 shown in FIG. 1 to FIG. 3.

The fluid-injector selective drive unit 60 can be fixed to a portion opposite to the multi-microneedle device 50 in the outer peripheral surface of the intermediate member 58e so as to be detachable, which is configured to selectively press the outside exposed end of the piston member 52c as described above. The structure can include a not-shown drive member abutting on the outside exposed end of the piston member 52c, a not-shown biasing force generation source applying a biasing force toward the outside exposed end of the piston member 52c to the drive member, and a switch mechanism allowing the not-shown biasing force generation source to selectively generate the biasing force.

More specifically, the not-shown biasing force generation source can be selected from, for example, a compression spring, a tension spring, an elastic material or a supply source of compressed gas including compressed air. Additionally, the switch mechanism can be a well-known latch mechanism, a trigger-type engagement release mechanism and a press-type engagement release mechanism which stop the movement of the not-shown drive member against the biasing force from the not-shown biasing force generation source, or a manual or electromagnetic drive on/off valve which can selectively supply the compressed gas from supply source of compressed gas including compressed air to the not-shown drive member.

First Modification Example

Figure 4:
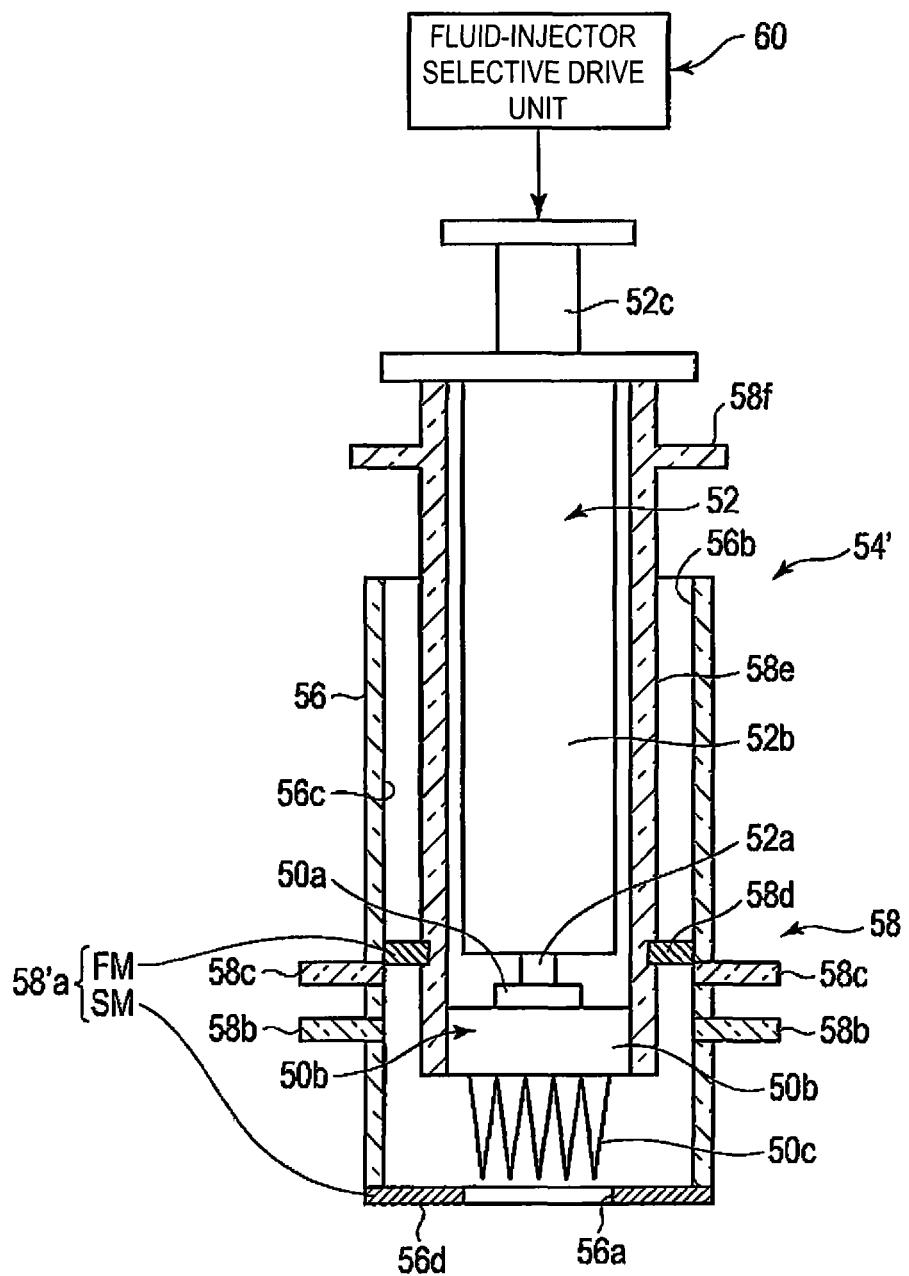
FIG. 4 is a schematic vertical-cross sectional view of an operation tool for the fluid injector using the multi-microneedle device according to a first modification example, in which the fluid injector using the multi-microneedle device is arranged in an initial position by a selective movement mechanism in the outer cylinder of the operation tool.

Next, a first modification example of the operation tool 54 according to the embodiment which has been shown in FIG. 1 to FIG. 3 will be explained with reference to FIG. 4.

Most of a structure of an operation tool 54' according to the first modification example is the same as that of the operation tool 54 according to the embodiment shown in FIG. 1 to FIG. 3. Accordingly, in the operation tool 54' according to the first modification example shown in FIG. 4, the same components as the components of the operation tool 54 according to the embodiment shown in FIG. 1 to FIG. 3 are denoted by the same reference codes, and the detailed explanation of these components is omitted.

The operation tool 54' according to the first modification example differs from the operation tool 54 according to the embodiment in the arrangement of a forcing unit 58'a in the fluid-injector housing space 56c of the outer cylinder 56. In the first modification example, the second magnetic force holding body SM of the forcing unit 58'a forms the end wall in which the one end opening 56a is formed as well as the skin contact surface 56d is presented in the outer cylinder 56.

Second Modification Example

Next, a second modification example of the operation tool 54 according to the embodiment which has been shown in FIG. 1 to FIG. 3 will be explained with reference to FIG. 5.

Most of a structure of an operation tool 54" according to the second modification example is the same as that of the operation tool 54 according to the embodiment shown in FIG. 1 to FIG. 3. Accordingly, in the operation tool 54" according to the second modification example shown in FIG. 5, the same components as the components of the operation tool 54 according to the embodiment shown in FIG. 1 to FIG. 3 are denoted by the same reference codes, and the detailed explanation of these components is omitted.

The operation tool 54" according to the second modification example differs from the operation tool 54 according to the embodiment in the arrangement of a forcing unit 58' in the fluid-injector housing space 56c of the outer cylinder 56 and the size of one end opening 56'a in the end wall of the outer cylinder 56.

The forcing unit 58"a according to the second modification example includes an outer-cylinder magnetic force holding body OM provided on the outer peripheral wall of the outer cylinder 56 and a fluid-injector magnetic force holding body RM arranged on the outer peripheral wall of the fluid injector 52 so that any one of the repulsion and an attraction force due to the magnetic force is generated between the fluid-injector magnetic force holding body RM and the outer-cylinder magnetic force holding body OM.

The outer-cylinder magnetic force holding body OM and the fluid-injector magnetic force holding body RM can be respectively magnets, can be magnetic bodies processed to hold the magnetic force and can be permeability magnetic materials into which small pieces or fine grains of magnets or magnetic bodies processed to hold the magnetic force are mixed.

In the second modification example, the fluid-injector magnetic force holding body RM is fixed in an inner side of the first and second stoppers 58*b* and 58*c* from the one end opening 56'*a* of the outer cylinder 56 on the outer peripheral surface of the intermediate member 58*e* for the fluid injector 52.

In the second modification example, the fluid-injector magnetic force holding body RM is fixed to the outer peripheral surface of the intermediate member 58*e* for the fluid injector 52 by well-known fixing means such as the adhesive, the fixing screw and fitting.

It is preferable that the fluid-injector magnetic force holding body RM is provided at least at one place on the outer peripheral surface of the intermediate member 58*e* for the fluid injector 52 as well as at plural places annularly arranged on the outer peripheral wall, and further, the entire fluid-injector magnetic force holding body RM may have an annular shape.

In the second modification example, the outer-cylinder magnetic force holding body OM is fixed in an inner side of the fluid-injector magnetic force holding body RM from the one end opening 56' *a* of the outer cylinder 56, namely, at a position closer to the other end opening 56*b* of the outer cylinder 56 in an inner surface of the outer peripheral wall of the outer cylinder 56 by well-known fixing means such as the adhesive, the fixing screw and the fitting, which generates the attraction force due to the magnetic force between the outer-cylinder magnetic force holding body OM and the fluid-injector magnetic force holding body RM.

It is preferable that the outer-cylinder magnetic force holding body OM is provided at least at one place on the inner surface of the outer peripheral wall of the outer cylinder 56 as well as at plural places annularly arranged on the inner surface of the outer peripheral wall of the outer cylinder 56, and further, the entire outer-cylinder magnetic force holding body OM may have an annular shape.

Figure 5:
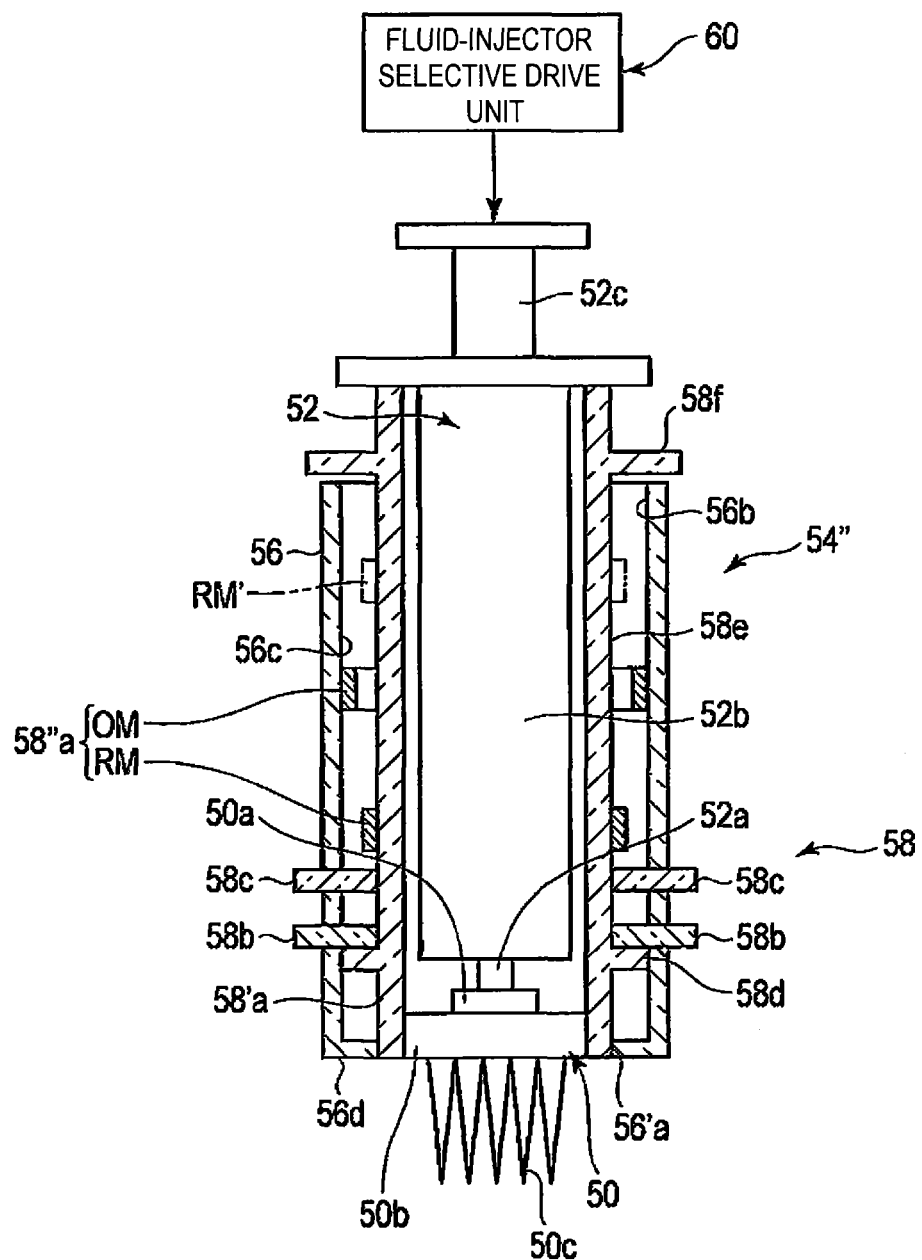
FIG. 5 is a schematic vertical-cross sectional view of an operation tool for the fluid injector using the multi-microneedle device according to a second modification example, in which the fluid injector using the multi-microneedle device is arranged in a first protruding position by a selective movement mechanism in the outer cylinder of the operation tool.

In the modification example, it is also preferable that a fluid-injector magnetic force holding body RM' is fixed at a position far from the one end opening 56'*a* of the outer cylinder 56, namely, a position close to the other end opening of the outer cylinder 56 in the inner surface of the outer peripheral wall of the outer cylinder 56 as compared with the outer-cylinder magnetic force holding body OM as shown by a two-dot chain line in FIG. 5 by using well-known fixing means such as the adhesive, the fixing screw and the fitting, which generates the repulsion due to the magnetic force between the fluid-injector magnetic force holding body RM' and the outer-cylinder magnetic force holding body OM.

The size of the outer cylinder 56 in a radial direction in the one end opening 56' *a* of the end wall of the outer cylinder of the operation tool 54" according to the second modification example is set to be slightly larger than the size of the outer cylinder 56 in the radial direction in the main body 50*b* of the multi-microneedle device 50.

Furthermore, a distance from the skin contact surface 56*d* in the end wall of the outer cylinder 56 to the first stopper 58*b* in the outer peripheral wall of the outer cylinder 56 is set to be shorter than a distance from the skin contact surface 56*d* in the end wall of the outer cylinder 56 according to the embodiment explained with reference to FIG. 1 to FIG. 3. As a result, in the second modification example, when the engaging portion 58*d* of the intermediate member 58*e* to which the multi-microneedle device 50 is fixed is engaged with the first stopper 58*b* arranged in the protruding position in the outer peripheral wall of the outer cylinder 56, and when the plural microneedles 50*c* of the multi-microneedle device 50 are held in the first protruding position as shown in FIG. 5 against any one of the attraction force and repulsion (biasing force) due to the magnetic force of the forcing unit 58"*a*, the main body 50*b* of the multi-microneedle device 50 pierces the one end opening 56'*a* of the end wall in the outer cylinder 56 of the operation tool 54', and an outer end surface of the main body 50*b* is substantially flush with the skin contact surface 56*d* of the end wall of the outer cylinder 56 of the operation tool 54".

In respective operation tool 54 according to the embodiment explained with reference to FIG. 1 to FIG. 3, the operation tool 54' according to the first modification example explained with reference to FIG. 4 and the operation tool 54" according to the second modification example explained with reference to FIG. 5, the engaging portion 58*d*, and the first magnetic force holding body FM, the fluid-injector magnetic force holding body RM or RM' of the forcing units 58*a*, 58'*a* and 58"*a* of the selective movement mechanism 58 are not directly formed on or are not directly fixed to the outer peripheral wall of the fluid holding cylinder 52*b* of the fluid injector 52, and formed on or fixed to the outer surface of the intermediate member 58*e* fixed to the fluid holding cylinder 52*b* through the multi-microneedle device 50 to which the fluid injector 52*b* is connected so as to be detachable. However, it is a matter of course that the intermediate member 58*e* is omitted and that the engaging portion 58*d*, and the first magnetic force holding body FM, the fluid-injector magnetic force holding body RM or RM' of the forcing units 58*a*, 58'*a* and 58'*a* of the selective movement mechanism 58 can be directly formed on or fixed to the outer peripheral wall of the fluid holding cylinder 52*b* of the fluid injector 52.

A multi-microneedle device in the medical field is considered to be used in an intradermal injection by being attached to the fluid outflow port of the injection cylinder in the conventional syringe instead of one injection needle which is well-known in the medical field. The multi-microneedle device includes a main body in which an outflow-port attaching port attached to the fluid outflow port for the fluid (liquid medicine in the medical field) of the injection cylinder so as to be detachable, and a fluid holding space temporarily holding the fluid flowing from the fluid outflow port of the injection cylinder to the outflow-port attaching port by pressing the piston member of the syringe are formed. The multi-microneedle device also has a plurality of microneedles arranged on a flat surface positioned on the opposite side of the outflow-port attaching port interposing the fluid holding space in the main body.

The flat surface of the main body functions as a skin contact surface, and respective plural microneedles have small fluid injection passages extending between a base end on the flat surface and tip ends apart from the flat surface. A length between the base end and the tip ends in respective plural microneedles (namely, the height of each microneedle) is set to be in a range of the thickness of skin tissue of living things (for example, all human beings) having skin tissue to be targets for use.

When the intradermal injection is performed by the syringe using the multi-microneedle device, a fluid (for example, liquid medicine) used for the intradermal injection is taken into the injection cylinder of the syringe in advance through the fluid outflow port of the injection cylinder. Next, the outflow-port attaching port of the multi-microneedle device is attached to the fluid outflow port of the injection cylinder so as to be detachable. After that, the air in the fluid holding space of the multi-microneedle device and the respective small fluid injection passages of plural microneedles is pushed out to an outer space by the fluid from the injection cylinder by slightly pushing the piston member of the syringe, thereby filling the fluid holding space of the multi-microneedle device and the respective small fluid injection passages of plural microneedles with the fluid.

Subsequently, the skin contact surface of the main body of the multi-microneedle device is pressed onto an exposed desired place of the skin of a living thing (for example, a human being). The plural microneedles on the skin contact surface pierce skin tissue of the exposed desired place of the skin of the living thing (for example, the human being) by the pressing. Next, when the piston of the syringe is subsequently pressed, the fluid from the injection cylinder is injected into the skin tissue of the desired exposed place of the skin of the living thing (for example, the human being) through the fluid holding space of the multi-microneedle device and the respective small fluid injection passages.

In the case where the intradermal injection is performed by the syringe using the multi-microneedle device, the piston member of the syringe is pushed while pressing the skin contact surface of the main body of the multi-microneedle device onto the exposed desired place of the skin of the living thing (for example, the human being). In this case, a pressure from the skin contact surface of the main body of the multi-microneedle device as well as a force of pushing the piston of the syringe are loaded on the exposed desired place of the skin, therefore, the skin tissue at the exposed desired place of the skin is compressed and elasticity of the skin tissue is somewhat lost. Accordingly, in the case where the intradermal injection is performed by the syringe using the multi-microneedle device, it was difficult to inject all of the fluid (for example, liquid medicine) from the plural microneedles to the skin tissue at the desired place, and the fluid was leaked to the surface of the desired place of the skin, or a relatively large amount of time was taken to inject all of the desired amount of fluid to the skin tissue at the desired place.

One aspect of the present invention is to provide an inexpensive operation tool with a simple structure, namely, an operation tool for a fluid injector using a multi-microneedle device which is capable of injecting all of a desired amount of fluid in the fluid injector into the skin tissue at a desired place for a short period of time easily as well as positively for anybody when an intradermal injection is performed in skin tissue at the desired place by the fluid injector such as a syringe using the multi-microneedle device.

According to one embodiment, there is provided an operation tool for a fluid injector using a multi-microneedle device including an outer cylinder having one end opening, the other end opening and a fluid-injector housing space extending between the one end opening and the other end opening, and holding the fluid injector using the multi-microneedle device so as to move along the center line in the longitudinal direction of the fluid injector, and a selective movement mechanism sequentially moving the fluid injector in the fluid-injector housing space of the outer cylinder among an initial position in which plural microneedles of the multi-microneedle device are retracted inside the fluid-injector housing space from the one end opening of the outer cylinder, a first protruding position in which the plural microneedles of the multi-microneedle device protrude to an outer space from the one end opening of the outer cylinder by a first given distance, and a second protruding position in which the plural microneedles of the multi-microneedle device protrude to the outer space from the one end opening of the outer cylinder by a second given distance shorter than the first given distance, in which a fluid flows from the fluid injector through the plural microneedles of the multi-microneedle device in the second protruding position.

The selective movement mechanism includes a forcing unit interposed between the outer cylinder and the fluid injector, forcing the fluid injector toward the initial position by a magnetic force, a first stopper provided in a first position a given distance apart from the one end opening of the outer cylinder toward the inside in an outer peripheral wall of the outer cylinder so as to be selectively extended/retracted in the fluid-injector housing space of the outer cylinder, a second stopper provided in a second position a given distance apart as compare with the first position from the one end opening of the outer cylinder toward the inside in the outer peripheral wall of the outer cylinder so as to be selectively extended/retracted with respect to the fluid-injector housing space of the outer cylinder, and an engaging portion protruding toward the outer peripheral wall of the outer cylinder in an outer peripheral wall of the fluid injector, and the engaging portion of the fluid injector is arranged in the initial position by a biasing force of the forcing unit without being engaged with the first and second stoppers while the first and second stoppers on the outer peripheral wall of the outer cylinder are arranged in the retracted position, the engaging portion of the fluid injector is engaged with the first stopper and the fluid injector is held in the first protruding position against the biasing force of the forcing unit as the first stopper is arranged in a protruding position after the fluid injector is moved to the first protruding position against the biasing force of the forcing unit, and the engaging portion of the fluid injector is engaged with the second stopper and the fluid injector is held in the second protruding position against the biasing force of the forcing unit when the first stopper is arranged in the retracted position as well as the second stopper is arranged in a protruding position after the fluid injector is moved to the first protruding position against the biasing force of the forcing unit.

In the operation tool for the fluid injector using the multi-microneedle device according to one embodiment, the fluid injector using the multi-microneedle device held in the fluid-injector housing space so as to move along the center line of the longitudinal direction of the fluid injector extending between the one end opening and the other end opening of the outer cylinder is sequentially moved among the initial position in which plural microneedles of the multi-microneedle device are retracted inside the fluid-injector housing space from the one end opening of the outer cylinder, the first protruding position in which the plural microneedles of the multi-microneedle device protrude to an outer space from the one end opening of the outer cylinder by a first given distance, and the second protruding position in which the plural microneedles of the multi-microneedle device protrude to the outer space from the one end opening of the outer cylinder by a second given distance shorter than the first given distance by the selective movement mechanism. A fluid flows from the fluid injector through the plural microneedles of the multi-microneedle device in the second protruding position.

In the first protruding position, the plural microneedles of the multi-microneedle device can be sufficiently inserted into skin tissue in a desired position. The skin contact surface of the main body of the multi-microneedle device can be sufficiently pressed onto the desired exposed position of a skin of a living thing.

At this time, a force of pressing the exposed desired position of the skin of the living thing by the plural microneedles of the multi-microneedle device reduces the elasticity of the exposed desired position of the skin. Then, this tendency is further increased when the skin contact surface of the main body of the multi-microneedle device is sufficiently pressed onto the exposed desired position of the skin of the living thing.

Next, in the second protruding position, the force of pressing the exposed desired position of the skin of the living thing by the plural microneedles of the multi-microneedle device can be alleviated. That is, the elasticity of the skin tissue in the exposed desired position of the skin is recovered. Then, this tendency is further increased when the skin contact surface of the main body of the multi-microneedle device contacts the exposed desired position of the skin of the living thing as described above.

When the fluid flows from the fluid injector through the plural microneedles of the multi-microneedle device in the second protruding position, the fluid flowing from the plural microneedles can be quickly injected into the skin tissue in the exposed desired position of the skin of the living thing.

Additionally, the movement from the initial position of the fluid injector using the multi-microneedle device with respect to the outer cylinder to the first protruding position as well as the movement from the first protruding position to the second protruding position can be easily and positively performed for anybody by operating the selective movement mechanism.

Accordingly, when the operation tool for the fluid injector using the multi-microneedle device according to one embodiment of the invention having the above structure is used, all of a desired amount of fluid in the fluid injector can be easily and positively injected by anybody into the skin tissue in the desired place for a short period of time in the case where the intradermal injection is performed to the skin tissue at the desired place by the fluid injector such as a syringe using the multi-microneedle device.

Furthermore, the above selective movement mechanism includes a forcing unit interposed between the outer cylinder and the fluid injector, forcing the fluid injector toward the initial position by a magnetic force, a first stopper provided in a first position a given distance apart from the one end opening of the outer cylinder toward the inside in an outer peripheral wall of the outer cylinder so as to be selectively extended/retracted in the fluid-injector housing space of the outer cylinder, a second stopper provided in a second position a given distance apart as compare with the first position from the one end opening of the outer cylinder toward the inside in the outer peripheral wall of the outer cylinder so as to be selectively extended/retracted with respect to the fluid-injector housing space of the outer cylinder, and an engaging portion protruding toward the outer peripheral wall of the outer cylinder in an outer peripheral wall of the fluid injector, and the engaging portion of the fluid injector is arranged in the initial position by a biasing force of the forcing unit without being engaged with the first and second stoppers while the first and second stoppers on the outer peripheral wall of the outer cylinder are arranged in the retracted position, the engaging portion of the fluid injector is engaged with the first stopper and the fluid injector is held in the first protruding position against the biasing force of the forcing unit as the first stopper is arranged in a protruding position after the fluid injector is moved to the first protruding position against the biasing force of the forcing unit, and the engaging portion of the fluid injector is engaged with the second stopper and the fluid injector is held in the second protruding position against the biasing force of the forcing unit when the first stopper is arranged in the retracted position as well as the second stopper is arranged in a protruding position after the fluid injector is moved to the first protruding position against the biasing force of the forcing unit.

The selective movement mechanism can be provided at low costs with a simple structure.

DESCRIPTION OF REFERENCE NUMERALS

50 multi-microneedle device
50a outflow-port attaching port
50b main body
50c microneedle
52 fluid injector
52a fluid outflow port
52b fluid holding cylinder
52c piston member
54 operation tool
56 outer cylinder
56a one end opening
57b other end opening
56c fluid-injector housing space
56d skin contact surface
58 selective movement mechanism
58a forcing unit
FM first magnetic force holding body
SM second magnetic force holding body
58b first stopper
58c second stopper
58d engaging portion
58e intermediate member
58f intermediate member operation protrusion
60 fluid-injector selective drive unit
SK skin
54' operation tool
58'a forcing unit
RM fluid-injector magnetic force holding body
OM outer-cylinder magnetic force holding body
54" operation tool
56'a one end opening
58"a forcing unit
RM' fluid-injector magnetic force holding body Obviously, numerous modifications and variations of the present invention are possible in light of the above teachings. It is therefore to be understood that within the scope of the appended claims, the invention may be practiced otherwise than as specifically described herein.

The invention claimed is:

1. An operation tool for a fluid injector having a multi-microneedle device, comprising:
an outer cylinder including a first open end, a second open end and a housing extending from the first open end to the second open end, the housing being formed such that a fluid injector having a multi-microneedle device is movable in the housing along a central line in a longitudinal direction of the fluid injector; and
a selective movement mechanism configured to move the fluid injector from an initial position to a first protruding position and then to a second protruding position in the housing of the outer cylinder, wherein the selective movement mechanism is configured such that, when the fluid injector is at the initial position, the multi-microneedle device has a plurality of microneedles retracted from the first open end of the outer cylinder and positioned inside the housing, when the fluid injector is at the first protruding position, the microneedles are protruded out to a first distance from the first open end, and when the fluid injector is at the second protruding position to discharge fluid through the microneedles of the multi-microneedle device, the microneedles are protruded out to a second distance from the first open end, the second distance being shorter than the first distance, the selective movement mechanism includes a forcing unit interposed between the outer cylinder and the fluid injector and configured to apply a magnetic force to the fluid injector toward the initial position, a first stopper positioned at a first position on an outer peripheral wall of the outer cylinder such that the first stopper is selectively extended into or retracted from the housing, the first position being at a distance away from the first open end toward the second open end, a second stopper positioned at a second position on the outer peripheral wall of the outer cylinder such that the second stopper is selectively extended into or retracted from the housing, the second position being at a distance away from the first position and toward the second open end, and an engaging portion provided on an outer peripheral wall of the fluid injector and protruding toward the outer peripheral wall of the outer cylinder, and the selective movement mechanism is configured such that, when the first and second stoppers are retracted from the housing, the engaging portion of the fluid injector initial position is not engaged with the first and second stoppers by a force of the forcing unit; when the first stopper is extended into the housing after the fluid injector is moved to the first protruding position against the force of the forcing unit, the engaging portion is engaged with the first stopper and the fluid injector is held in the first protruding position against the force of the forcing unit; and when the first stopper is retracted from the housing and the second stopper is extended into the housing after the fluid injector is moved to the first protruding position against the force of the forcing unit, the engaging portion is engaged with the second stopper and the fluid injector is held at the second protruding position against the force of the forcing unit.

2. The operation tool according to claim 1, wherein the forcing unit includes a first magnetic force holding body provided in the engaging portion of the fluid injector and a second magnetic force holding body provided on the outer cylinder such that the magnetic force causes repulsion between the first and second magnetic force holding bodies.

3. The operation tool according to claim 2, wherein each of the first and second magnetic force holding bodies includes a magnet.

4. The operation tool according to claim 3, further comprising:

a fluid-injector selective drive unit configured to allow the fluid held by the fluid injector to flow through the multi-microneedle device by selectively driving the fluid injector.

5. The operation tool according to claim 2, further comprising:

a fluid-injector selective drive unit configured to allow the fluid held by the fluid injector to flow through the multi-microneedle device by selectively driving the fluid injector.

6. The operation tool according to claim 1, wherein the forcing unit includes an outer-cylinder magnetic force holding body provided on the outer peripheral wall of the outer cylinder and a fluid-injector magnetic force holding body provided on the outer peripheral wall of the fluid injector such that the magnetic force causes attraction or repulsion between the outer-cylinder magnetic force holding body and the fluid-injector magnetic force holding body.

7. The operation tool according to claim 6, wherein each of the outer-cylinder magnetic force holding body and the fluid-injector magnetic force holding body includes a magnet.

8. The operation tool according to claim 7, further comprising:

a fluid-injector selective drive unit configured to allow the fluid held by the fluid injector to flow through the multi-microneedle device by selectively driving the fluid injector.

9. The operation tool according to claim 6, further comprising:

a fluid-injector selective drive unit configured to allow the fluid held by the fluid injector to flow through the multi-microneedle device by selectively driving the fluid injector.

10. The operation tool according to claim 1, further comprising:

a fluid-injector selective drive unit configured to allow the fluid held by the fluid injector to flow through the multi-microneedle device by selectively driving the fluid injector.

* * * * *